United States Patent
O'Dwyer et al.

[19]

[11] Patent Number: 6,100,529
[45] Date of Patent: Aug. 8, 2000

[54] AUTOMATIC PORTABLE AUTOMOTIVE REFRIGERANT ANALYZER

[75] Inventors: Barry O'Dwyer, Marlborough, N.H.; Christopher D. Prozzo, Athens, Vt.

[73] Assignee: Janos Technology Inc., Townshend, Vt.

[21] Appl. No.: 08/994,351

[22] Filed: Dec. 19, 1997

[51] Int. Cl.[7] .................................................. G01N 21/35
[52] U.S. Cl. ................ 250/343; 250/339.13; 250/339.12
[58] Field of Search .............................. 250/343, 339.13, 250/339.12

[56] References Cited

U.S. PATENT DOCUMENTS 5,610,398   3/1997   Anderson et al. ................. 250/339.12
5,672,874   9/1997   Fujii et al. ......................... 250/339.12

*Primary Examiner*—Constantine Hannaher
*Assistant Examiner*—Andrew Israel
*Attorney, Agent, or Firm*—Herbert M. Wolfson

[57] ABSTRACT

An automatic no moving parts portable IR spectrometer for the purpose of analyzing automotive refrigerants comprising an IR source with intermittent output by electronic means not requiring an optical cavity or mechanical chopper, a gas cell which is activated via a one touch bellows to initiate a pressure switch triggering the analysis process, said gas cell followed by a non-imaging optical element which diverts the IR energy to a filter and detector equipped with a readout device to show analysis results.

1 Claim, 2 Drawing Sheets

AUTOMATIC PORTABLE AUTOMOTIVE REFRIGERANT ANALYZER

FIELD OF INVENTION

A device to determine the concentration of refrigerant gases utilized in automotive refrigerant systems.

BACKGROUND OF INVENTION

In the past several decades there have been many designs investigated for the use of infrared spectroscopic instruments for the analysis of gases. The majority of these instruments have utilized one or more filters in order to select an analytical frequency for the detection of a specific gas or gases. The source is selected from various heated elements from 800 to 1000° C. which give a broad band of IR energy continuous from 2–15 microns. The energy emitted by the heated element, termed the source, is customarily "chopped", i.e. intermittently interrupted by a mechanical means, which constitutes a moving part.

The gas mixture or single component is contained in a cell, a metal or glass tube fitted with IR transmitting windows, as sodium chloride, etc., with inlet and outlet pipe to give entry and egress to the gas or gases to be analyzed; this act of filling and emptying the gas cell requires a pump with moving parts.

In addition to the components comprising a modern filter IR spectrometer intended for the analysis of single or multiple gases, it is, of course, essential to have a filter or an array of filters with a suitable optical system to focus light from the source onto said filter or filter array, and thence to a detector or array of detectors in order to generate an electrical signal proportional to the concentration of the species to be analyzed. Said electrical signal is processed via a micro-processor which is calibrated by means of conducting analysis on gas mixtures of known composition and the result suitably displayed by means of a graph CRT screen, LED display or the like.

By a critical examination of each of the above elements of today's classic gas analyzer, we have discovered a simple, accurate device for the analysis of a gas sample without moving parts, without complex optical systems, capable of economic manufacture and eminently portable.

SUMMARY OF INVENTION

The key to a new and novel device for gas analysis by IR spectroscopy lies in the selection of a superior source. It has now been determined that the type of glower element utilized in diesel engines in order to initiate combustion in the start-up phase of the engine operation represents an ideal IR energy source. The intermittent operation of such a source is easily facilitated by means of a simple FET circuit. The cycle time is 1 to 3 hertz per second, thus allowing for a suitable period of on-off time for energy striking the detector.

The energy output from such a source is adequate to the functionality of not only the source, but is sufficiently directed to not require an optical system to concentrate the passage of energy from the source to the detector element. Since the IR energy beam is very concentrated geometrically, no lenses, mirrors, beam splitters, etc. are needed as auxiliary optical elements. The facilitated source on-off function requires no moving parts of an auxiliary nature. The gas in-out function is performed by a simple bellows in the gas inlet outlet system in order to place the new gas sample in the gas cell. This is done by a simple thumb press of the bellows located on the face of the instrument.

The currently available small IR filters and equally small IR detectors, both only 3–4 mm in diameter, means that they make possible a very small gas analyzer.

The inclusion of a micro-processor in order to perform the calculations constitutes a minor task, and read-out can be LCD, printer, status lights and the like.

The device can be made portable as it requires very low voltage, having no electronic pumps or motors.

BRIEF DESCRIPTION OF FIGURES

FIG. 1 Legend
1—line to power supply
2—FET circuitry to pulse source
3—power to source
4—glow plug source
5—path of IR light
6—line from automotive refrigerant supply
7—bellows to clear gas cell of sample
8—inlet line to gas cell
9—gas cell with windows of an IR transmitting material
10—outlet pipe from gas cell
11—combination cylinder and/or cone to concentrate IR light on filter(s).
12—multiple filters, or single filter, or multi band filter
13—detector, IR sensitive
14—line to micro-processor—display
15—micro-processor FIG. 2 Legend
4—glow plug
16—housing
17—gasket
18—BaF2 window
10—gas pipe out
19—BaF2 window
12—band pass filters
13—detectors
20—heat sink
8—gas pipe in

DETAILED DESCRIPTION OF THE INVENTION

Figure 1:
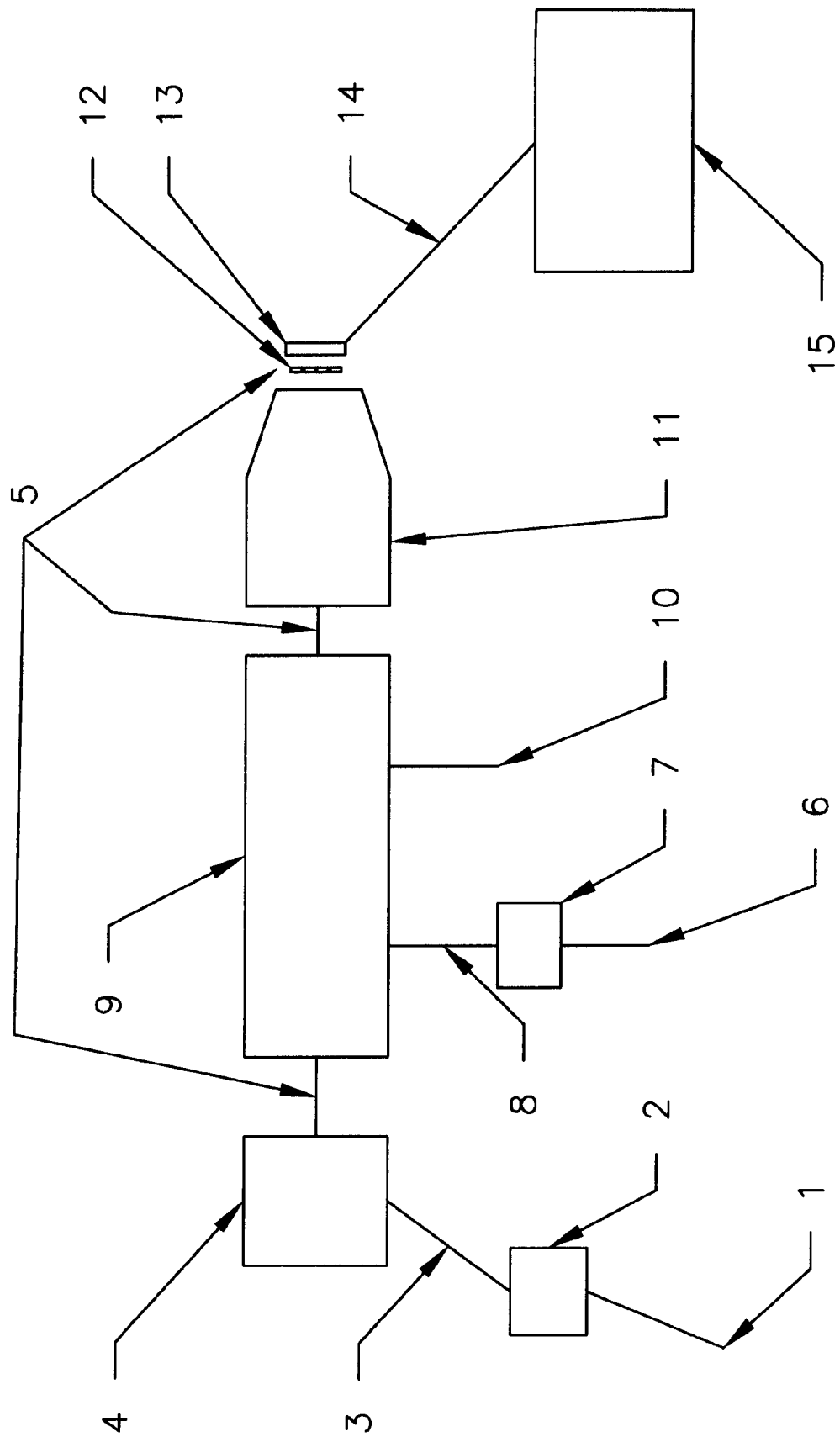
FIG. 1 is a schematic view of the portable analyzer.

A general overview of the gas analyzer is shown in FIG. 1, in 1 is the power cord leading to the circuitry 2, which pulses the source 3. This use of electronic pulsing at a controlled frequency is an ideal replacement for a mechanical chopper and avoids the use of moving parts. The source 3 is a glow plug-type of device commonly used to initiate combustion in small gas engines, or diesel engines. This source generates a very intense beam of IR energy and make unnecessary the use of auxiliary concentrating optics, such as mirrors, beam splitters and lenses. All optical elements involved are grouped on a narrow axial path which makes possible a miniature hand held class of gas detectors which can be truly portable.

The IR energy 5 indicates the path of the IR light. The inlet line to the gas cell 6 which is integrally linked to the automotive air conditioning system which furnishes the requisite pressure for propelling the gas to be measured. A small bellows 7 which is manually operated by one touch which displaces the gas in the gas cell with an air sample provides pressure to a pressure switch which initiates the zeroing and the measurement cycle. The inlet pipe 8, and outlet pipe 10 furnish a flow of gas to the gas cell 9 which has barium fluoride windows which are not attacked by moisture. An optional element is a non-imaging cylinder—cone 11, which concentrates IR energy on the filter array 12 which can be singular or possess a multiplicity of discreet IR filters. Light which has transited the filters impacts on a detector 13 giving a signal which is conveyed to the amplifier—micro-processing unit 15 by the cable 14. A suitable display, not shown, displays concentration values in suitable units and data can be stored as desired.

Figure 2:
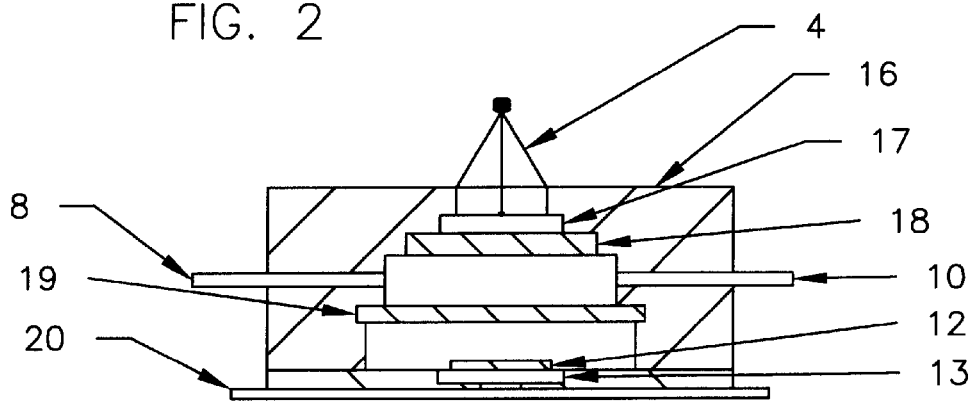
FIG. 2 is a side view of the portable analyzer.

FIG. 2 depicts a more detailed view of the gas analysis device in which the source 4 is held in position by means of a metal container 16. A gasket 17 isolates the source from the gas cell, whose inlet and outlet connections are shown as 10 and 8 respectively. The barium fluoride windows are labeled 18 and 19 respectively and are chemically quite inert to any gases expected to be present in the samples to be analyzed. The band pass filter 12, which can be singular or a multiplicity of filters selected for the analysis of the singular or multiple gases to be analyzed. The detector 13 is held in position by the heat sink 20. The connecting line from the heat sink to the central processing unit is not shown.

The unit is calibrated for analysis via the utilization of mixtures of known concentrations of the several gases to be analyzed at the point of manufacture. The calibration data necessary to perform and display the concentrations of the gas samples to be analyzed are stored in memory in the central processing unit. The processor routine and the program for this analysis are well known to those in this art.

The composition of the gas mixture or single component is not limited to a singular type, but can include any mixture of organic or inorganic gases which possess an inherent capability for the absorption of IR energy. Absorption bands or discreet IR ranges can be selected to identify a characteristic absorption of a particular species, and IR bandpass filters can be manufactured to pass said bands to the detectors while blocking IR energy generally outside said bands.

This device, herein described, is suitable for the analysis of automotive gases, both refrigerant and exhaust, and it can easily be adapted for the analysis of other gases, liquids or solids. Classical IR liquid cells which are items of commerce could replace the gas cell 9 when liquids are to be analyzed. Solids, singular or multiple component, could be similarly analyzed by placing the components in solution and placing in an IR liquid cell, as previously described. Film samples can be analyzed in a direct fashion simply by intersecting the IR energy beam. Solid samples can also be quantitatively measured by employing Attenuated Total Reflectance (ATR) techniques by placing an ATR crystal in the IR beam pathway and bringing the sample into optical contact with the ATR crystal.

What is claimed is:

1. In a system for analyzing one or more automotive gases which comprises (1) an infrared light source to transmit a beam of infrared light intermittently through (2) a gas cell containing the gas or gases to be analyzed, then through (3) one or more filters of predetermined wavelengths to (4) one or more detectors, each sensitive to a different predetermined wavelengh range of inflated light, the output of the detectors transmitted to (5) a processor which converts the energy received from the detectors into concentrations of each of the gases in the automotive gas supplied to the gas cell, the improvement which comprise, a glow-plug device that is used to initiate combustion in a small gas or diesel engine as said infrared light source.

* * * * *